United States Patent [19]

Goosen

[11] Patent Number: Plant 5,388

[45] Date of Patent: Jan. 15, 1985

[54] PEACH PLANT

[76] Inventor: Raymond Goosen, 5327 Ave. 400, Dinuba, Calif. 93618

[21] Appl. No.: 509,878

[22] Filed: Jul. 1, 1983

[51] Int. Cl.[3] ..... A01H 5/03

[52] U.S. Cl. ..... Plt./43

[58] Field of Search ..... Plt./43

*Primary Examiner*—Robert E. Bagwill

*Attorney, Agent, or Firm*—Vergil L. Gerard

[57] ABSTRACT

Disclosed is a new and distinct peach plant having the cultivar name Ray Crest, broadly characterized by early picking date between May 21 and 24, a full 7 days earlier than the parent plant, Springcrest (unpatented), and having a semi-free stone which parts freely from the flesh when fully ripe, medium to large size fruit for season of maturity, with 50–90% overlay of blush to dark red coloration somewhat mottled with longitudinal streaking of dark red. The tree is large, vigorous, productive and hardy for California conditions. For eating, early shipping and fresh market with good keeping and shipping quality.

1 Drawing Figure

1

Disclosed is a new and distinct peach tree having the cultivar name Ray Crest and generally characterized as being large, vigorous, productive, hardy for California conditions, and regularly bearing fruit of excellent size for the early season of maturity, and by yellow flesh, semi-free stone, and good eating and shipping quality.

The instant plant originated in Tulare County (San Joaquin Valley), Calif., as an early ripening sport and an improvement on the parent plant, Springcrest (unpatented), by ripening a full 7 days earlier, and an improvement on Maycrest (U.S. Plant Pat. No. 4,064), also an early maturing sport of Springcrest, by ripening a full 3 days earlier. It has been asexually reproduced by me by budding and found true to form in all respects.

The tree blooms slightly early for the season and sets flower buds which are hardy for California conditions. Picked at commercial maturity, the first picking date when described was May 21, 1982, and the last picking date May 24, 1982. The fruit is medium to large for season of maturity, measuring (B×W×L) 64×66×67 mm. The skin is nearly free from flesh when soft ripe with no observed tendency to crack, and has a yellow ground color with 50% to 90% of the surface overlain with blush to dark red, with blush somewhat mottled with longitudinal streaking of dark red. The flesh is totally yellow by commercial maturity. Amygdalin is moderate, juice abundant and moderately rich at full maturity, texture is firm, fine and melting with new fibers. Flavor is mild with distinct aroma. The stone parts freely from flesh when fully ripe. The present invention relates to a peach tree and more particularly to a new and distinct variety broadly characterized by a large, vigorous, productive and regular bearing tree, early ripening fruit of excellent size for the early season of maturity, and by yellow flesh, semi-free stone, and good eating and shipping quality.

The instant variety most nearly resembles its parent plant, Springcrest (unpatented), but is an improvement thereon by ripening a full seven days earlier, and Maycrest (U.S. Plant Pat. No. 4,064), also an early maturing sport of Springcrest, but an improvement thereon by ripening a full three days earlier.

The present variety of peach tree originated in a bearing orchard of Springcrest (unpatented) peaches owned by me in Tulare County, Calif., by appearing as an early ripening mutuation involving a full scaffold

2 limb. The mutation was then asexually reproduced by budding in May, 1979, and by subsequently planting the developed trees in the same area. The reproductions of the plant and fruit characteristics were true to the original mutuation in all respects.

The accompanying photograph shows the characteristics of the whole fruit in skin color and form, and a characteristic fruit divided at its suture plane showing the flesh color and stone. de Referring now more specifically to the pomological characteristics of this new and distinct variety of peach tree, the following has been observed under the ecological conditions prevailing near Dinuba, Tulare Count, Calif. All major color plate identifications are by reference to Maerz and Paul Dictionary of Color, 1950 Ed.

TREE

General: Large, vigorous, upright, spreading, hardy for California conditions, with shape and density determined by pruning.

Productivity: Productive and regular bearing.

Trunk: Medium thickness and medium surface texture.

Branches: Medium diameter and average surface texture. Color of young branches brownish (7-E-11), current season's light green (19-I-6). Lenticels numerous.

Leaves: Large in size. Average leaf size determined from leaves at midpoint of actively growing shoots. Average length 21.0 cm., width 4.5 cm. Form lanceolate, leaf apex acute to slightly acuminate. Leaves of average thickness, upper surface dark green in color (24-L-7), lower surface lighter (22-H-7). Leaf surface relatively smooth, margin finely crenate, slightly wavy, apex usually recorved and moderately twisted. Petiole moderately long, average 15 mm., and of medium thickness. Glands irregularly 3 to 5 in number, usually alternate in position. Medium size, globose. Gland surface yellowish (17-K-3) when immature but darkening with age. Glands generally borne on short stalk; typically 2 to 3 located on petiole and 1 to 2 on leaf base. Stipules light green (20-J-6), 11 to 14 mm in length. Early deciduous.

FLOWERS

Flower buds: Hardy for California conditions. Medium size, free from stem, plump and moderately pubescent.

Flowers: Bloom date slightly early for season. Large, showy.

FRUIT

Maturity when described: At commercial maturity; firm ripe. First picking May 21, 1982, last picking May 24, 1982. Full crop.

Size: Uniform, medium to large for season of maturity; average axial diameter 64 mm, average right angle to suture plane 66 mm, average suture plane 67 mm.

Form: Uniform, globose in axial aspect. Generally symmetrical. Globose to slight oblate in ventral suture aspect. Symmetrical to slightly uneven.

Suture: Usually a distinct yellow continuous line, 1 to 3 mm in width without red coloration, extending from base to within 6 to 10 mm of the apex. Occasionally a slight depression beyond pistil point. Final 20 mm of basal portion of suture moderately creased.

Ventral surface: Rounded, very slightly lipped on right or left side. Lips at times unequal but only slightly so.

Stem cavity: Axial aspect rounded to slightly elongated in suture plane, with suture visible on ventral side only. Cavity 19–23 mm wide, 28–32 mm long; cavity broadly conic, 11–14 mm deep.

Base: Rounded to slightly truncated, at right angle to the fruit axis.

Stem: Medium length, 10–14 mm.

Apex. Rounded. Pistil point apical to occasionally oblique.

Skin: Medium thickness, medium texture, nearly free from flesh when fruit at soft ripe maturity. No observed tendency to crack.

Skin color: At commercial harvest maturity ground color yellow (18-K-1). 50 to 90 percent of fruit surface overlain with blush red (5-K-10) to dark red (6-K-5) depending on fruit exposure and state of maturity. Blush somewhat mottled with longitudinal streaking of dark red (6-K-5).

Pubescence: Moderate, short, rolls up when rubbed.

Flesh color: Yellow (10-K-5). No red in flesh at commercial maturity.

Surface of pit cavity: Yellow (10F-2) with numerous white fibers on surface.

Amygdalin: Moderate.

Juice: Abundant and moderately rich when at full maturity.

Texture: Firm, fine, melting.

Fibers: Few, fine tender.

Flavor: Mild with distinct aroma. Ripens evenly. Eating quality good.

STONE

Tenacity to flesh: Semi-free, parts freely from flesh when fully ripe.

Size: Medium. Average thickness (breadth) 17–19 mm. Average width 24–26 mm. Average length 34–37 mm.

Ratio (B-W-L): Instant variety, $1 \times 1.4 \times 2.0$. Maycrest (U.S. Plant Pat. No. 4,064), $1 \times 1.3 \times 9$.

Form: Ovate in lateral aspect with wing strongly protruding from basal third of ventral suture.

Hilum: Oval, fairly narrow.

Base: Slightly oblique from central axis sloping to ventral suture.

Apez: Acute to acuminate, tip guide sharp.

Sides: Variable but most often nearly equal.

Surface: Regularly furrowed near base and toward apex. Pitted throughout central area (lateral aspect).

Ridges: Broad, somewhat flattened and smooth on top.

Pits: Variable in shape, circular to oval.

Ventral edge: Medium thickness with strong protruding wing along basal third suture. Short wings in central suture area often more strongly developed on one side.

Dorsal edge: Broad with deep wide groove extending from base up to $\frac{3}{4}$ of entire length of dorsal suture. Edge near apex moderately eroded down $\frac{1}{4}$ of full length of suture. Ridges along edge of suture deeply grooved and converging basally.

Color: Buff (9-J-5).

Eating, early shipping variety, fresh market. Good keeping quality, good shipping quality.

Having thus described and illustrated my new variety of peach tree, what is claimed is:

1. A new and distinct variety of peach substantially as described and illustrated, which is characterized by a vigorous, regular bearing tree hardy for California conditions, very early ripening fruit with blush to dark red mottling and longitudinal red streaking over yellow ground color, large size for its early season, semi-free stone, and globose form, and which most closely resembles its parent plant, Springcrest (unpatented) and Maycrest (U.S. Plant Pat. No. 4,064), also an early maturing sport of Springcrest, but is distinguished therefrom by reaching commercial maturity 7 days earlier than Springcrest and 3 days earlier than Maycrest.

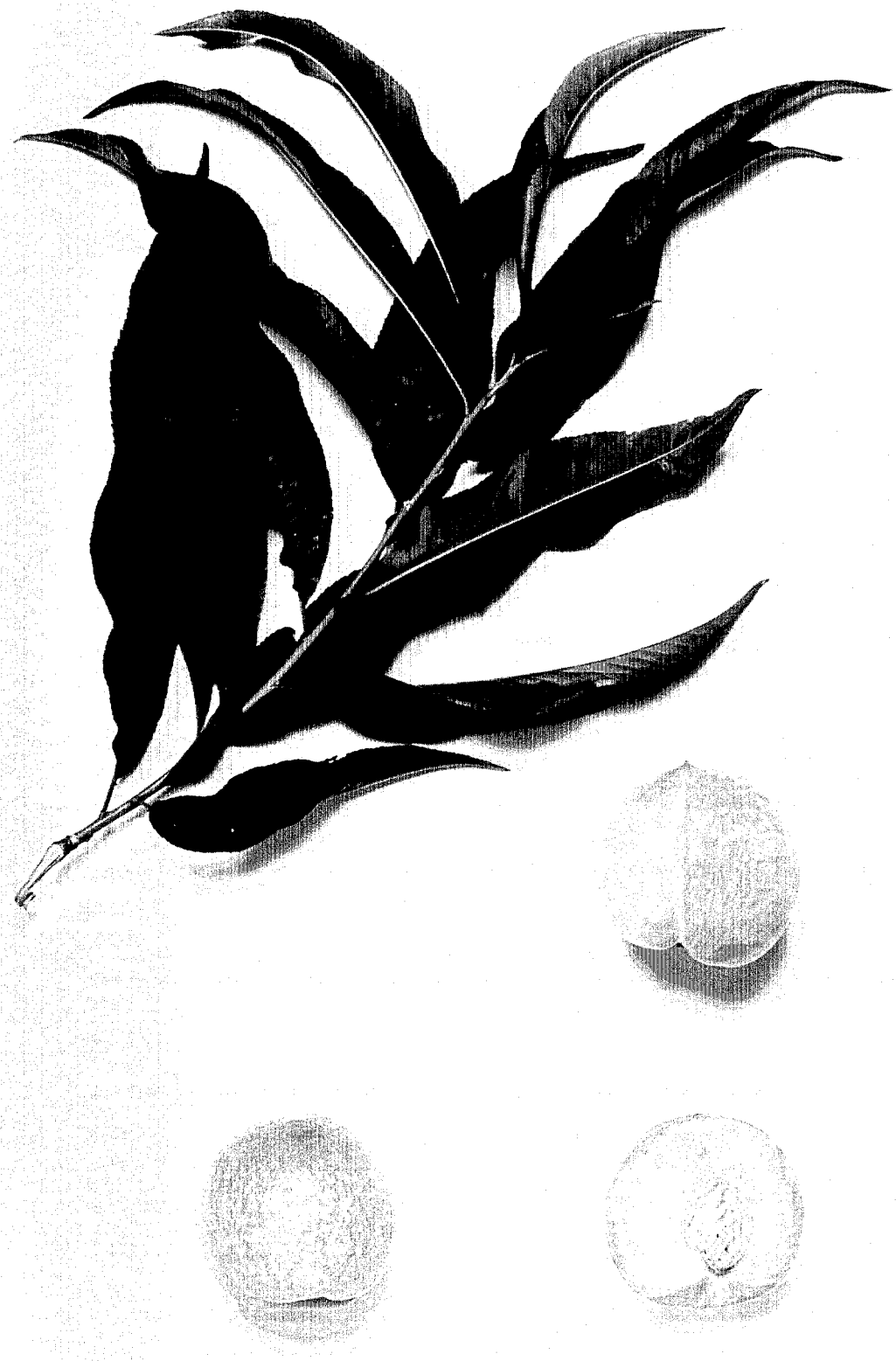

* * * * *